United States Patent [19]
Dow et al.

[11] Patent Number: 5,859,044
[45] Date of Patent: Jan. 12, 1999

[54] β-ADRENERGIC AGONISTS

[75] Inventors: Robert L. Dow, Waterford; Kristin M. Lundy, Groton, both of Conn.

[73] Assignee: Pfizer Inc., New York, N.Y.

[21] Appl. No.: 892,381

[22] Filed: Jul. 14, 1997

Related U.S. Application Data

[60] Provisional application No. 60/022,827 Jul. 31, 1996.

[51] Int. Cl.$^6$ .......................... A61K 31/40; C07D 209/42
[52] U.S. Cl. ............................................ 514/419; 548/492
[58] Field of Search .............................. 548/492; 514/419

[56] References Cited

U.S. PATENT DOCUMENTS 5,627,200  5/1997  Kreutter et al. ......................... 514/367

OTHER PUBLICATIONS

Berkowitz et al., "Distribution of B3–Adrenoceptor mRNA in Human Tissues," European Journal of Pharmacology, vol. 289, pp. 223–228, 1995.
Hoffstedt et al., "Effects of several putative Beta3–adrenoceptor agonists on lipolysis in human omental adipocytes," Chemical Abstracts, vol. 125, No. 7, p. 112, 1996.
Sinkula, "Prodrug Approach in Drug Design," Medicinal Chemistry, 1975, vol. 10, pp. 306–315.
Krief et al., "Tissue Distribution of Beta3–adrenergic Receptor mRNA in Man," Journal of Clinical Investigation, vol. 91, 1993, pp. 344–349.
Taneja et al., "Evidence for a Noradrenergic Innervation to Atypical Beta Adrenoceptors in the Ileum of Guinea Pig," Journal of Pharmacology and Experimental Therapeutics, vol. 260, No. 1, pp. 192–199, 1992.
Giudice et al., "Inhibition of Rat Colonic Motility and Cardiovascular Effects of New Gut–Specific Beta–adrenergic Phenylethanolaminotetralines," Life Sciences, vol. 44, pp. 1411–1417, 1989.

*Primary Examiner*—Mukund J. Shah
*Assistant Examiner*—Ann M. Kessinger
*Attorney, Agent, or Firm*—Peter C. Richardson; Gregg C. Benson; Robert T. Ronau

[57] ABSTRACT

The present invention relates to certain compounds of the formula (I) the racemic-enantiomeric mixtures and optical isomers of said compounds, prodrugs thereof and the pharmaceutically acceptable salts, depicted below, which are β-adrenergic receptor agonists and accordingly have utility as, inter alia, hypoglycemic and antiobesity agents. The invention also relates to methods of use for the compounds and to compositions containing them. The compounds of the present invention also possess utility for increasing lean meat deposition and/or improving the lean meat to fat ratio in animals, e.g., ungulate animals, companion animals, especially dogs, and poultry. The compounds of formula (I) have the following structure

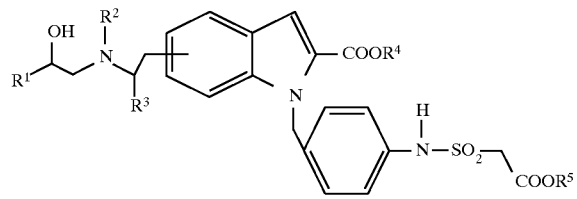

wherein $R^1$, $R^2$, $R^3$, $R^4$ and $R^5$ are as defined in the specification.

20 Claims, No Drawings

β-ADRENERGIC AGONISTS

This application was filed under 35 U.S.C. §111 based on provisional application No. 60/022,827 which was filed on Jul. 31, 1996.

BACKGROUND OF THE INVENTION

The present invention relates to certain compounds of the formula (I) depicted below, which are β-adrenergic receptor agonists and accordingly have utility as, inter alia, hypoglycemic and antiobesity agents. More specifically, the compounds of the instant invention are selective agonists of the $\beta_3$-adrenergic receptor. The invention also relates to methods of use for the compounds and to compositions containing them. The compounds of the present invention also possess utility for increasing lean meat deposition and/or improving the lean meat to fat ratio in animals, e.g. ungulate animals, companion animals, especially dogs, and poultry.

The compounds of this invention further possess utility in the treatment of intestinal motility disorders, depression, prostate disease, dyslipidemia, and airway inflammatory disorders such as asthma and obstructive lung disease.

The disease diabetes mellitus is characterized by metabolic defects in production and utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The compounds of the present invention and the pharmaceutically acceptable salts thereof effectively lower blood glucose levels when administered to mammals with hyperglycemia or diabetes.

The compounds of the present invention also reduce body weight or decrease weight gain when administered to animals. The ability of these compounds to affect weight gain is due to activation of $\beta_3$-adrenergic receptors which stimulate the metabolism of adipose tissue.

β-Adrenergic receptors have been categorized into $\beta_1$-, $\beta_2$- and $\beta_3$-subtypes. Agonists of β-receptors promote the activation of adenyl cyclase. Activation of $\beta_1$-receptors invokes increases in heart rate while activation of $\beta_2$-receptors induces relaxation of skeletal muscle tissue which produces a drop in blood pressure and the onset of smooth muscle tremors. Activation of $\beta_3$-receptors is known to stimulate lipolysis (the breakdown of adipose tissue triglycerides to glycerol and free fatty acids) and metabolic rate (energy expenditure), and thereby promote the loss of fat mass. Compounds that stimulate $\beta_3$-receptors are therefore useful as anti-obesity agents, and can also be used to increase the content of lean meat in animals. In addition, compounds which are $\beta_3$-receptor agonists have hypoglycemic or anti-diabetic activity, but the mechanism of this effect is uncertain.

Until recently $\beta_3$-adrenergic receptors were thought to be found predominantly in adipose tissue. $\beta_3$-receptors are now known to be located in such diverse tissues as the intestine (J. Clin. Invest, 91, 344 (1993)) and the brain (Eur. J. Pharm., 219,193 (1992)). Stimulation of the $\beta_3$-receptor has been demonstrated to cause relaxation of smooth muscle in colon, trachea and bronchi. Life Sciences, 44(19), 1411 (1989); Br. J. Pharm., 112, 55 (1994); Br. J. Pharmacol., 110, 1311 (1993). For example, stimulation of $\beta_3$-receptors has been found to induce relaxation of histamine-contracted guinea pig ileum, J. Pharm. Exp. Ther., 260, 1, 192 (1992).

The $\beta_3$-receptor is also expressed in human prostate. Because stimulation of the $\beta_3$-receptor causes relaxation of smooth muscles that have been shown to express the $\beta_3$-receptor (e.g., intestine), one skilled in the art would predict relaxation of prostate smooth muscle. Therefore $\beta_3$-agonists are useful for the treatment or prevention of prostate disease.

U.S. Pat. No. 5,061,727 concerns certain substituted 5-(2-((2-aryl-2-hydroxyethyl)amino)-propyl)-1,3-benzodioxoles which are disclosed to possess anti-diabetic and/or anti-hyperglycemic and/or anti-obesity properties.

European Patent publication 516,349, published Dec. 2, 1992, refers to certain 2-hydroxyphenethyl amines which possess antiobesity, hypoglycemic and related utilities.

U.S. Pat. No. 4,358,455 is concerned with certain heterocyclic compounds of the formula Het-CHOH—CH$_2$—NH-aralkyl, useful for treating glaucoma and cardiovascular disorders.

U.S. Pat. No. 5,030,640 concerns certain α-heterocyclic ethanol amino alkyl indoles, useful as growth promoters, bronchodilators, antidepressants and antiobesity agents.

U.S. Pat. No. 5,019,578 concerns certain α-heterocyclic ethanol amines useful as growth promoters.

SUMMARY OF THE INVENTION

This invention relates to compounds having the formula I

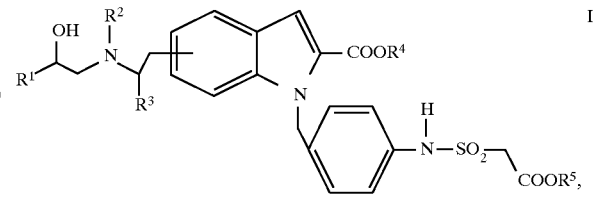

the racemic-enantiomeric mixtures and optical isomers of said compounds, prodrugs thereof and pharmaceutically acceptable salts thereof,
wherein
$R^1$ is an optionally substituted phenyl, phenoxyalkyl having 1 to 4 carbons in the alkyl portion where the phenoxy portion is optionally substituted, optionally substituted pyridinyl, optionally substituted pyrimidyl, optionally substituted thiazolyl or optionally substituted oxazolyl;
where the optionally substituted moieties of $R^1$ are optionally substituted with one to three substituents, each substituent is independently selected from the group consisting of hydroxy, fluoro, chloro, iodo, bromo, nitro, $CF_3$, cyano, sulfonamide, $(C_1–C_6)$alkyl optionally independently substituted with one or more halo atoms, $(C_1–C_6)$alkoxy optionally independently substituted with one or more halo atoms, carboxy, hydroxyalkyl, $(C_1–C_4)$alkoxycarbonyl, $(C_1–C_6)$alkylthio, sulfonyl, sulfinyl, —$NX^1X^2$, —NH—CO—$(CH_2)_a$-(phenyl), —NH—CO—$(C_1–C_{10})$alkyl, —NH—$SO_2$—$(CH_2)_a$-(phenyl) and —NH—$SO_2$—$(C_1–C_{10})$alkyl;

a for each occurrence is independently 0, 1, 2, 3 or 4;
$X^1$ and $X^2$ for each occurrence are each independently hydrogen, $(C_1-C_6)$alkyl, $(C_1-C_8)$alkoxy$(C_1-C_6)$alkyl, or $(C_3-C_8)$cycloalkyl, or $X^1$ and $X^2$ are taken together with the nitrogen atom to which they are attached and form a saturated heterocyclic ring having from 3 to 7 carbon atoms where one of said carbon atoms of said saturated heterocyclic ring is optionally replaced by oxygen, nitrogen or sulfur;
$R^2$ is hydrogen or $(C_1-C_6)$alkyl;
$R^3$ is hydrogen or $(C_1-C_6)$alkyl optionally independently substituted with one or more halo atoms;
$R^4$ is hydrogen or $(C_1-C_4)$alkyl optionally independently substituted with one or more halo atoms; and
$R^5$ is hydrogen or $(C_1-C_4)$alkyl.

The present invention also relates to pharmaceutical compositions, useful for treating a condition, disease, or disorder in a mammal, including any of the conditions, diseases and/or disorders disclosed herein, comprising an amount of a compound of formula I as defined hereinabove, Compounds which are preferred among the Group B compounds, designated "Group C", are those compounds of Group B wherein $R^3$ is $(C_1-C_6)$alkyl.

Compounds which are preferred among the Group C compounds, designated "Group D", are those compounds of Group C wherein $R^4$ is hydrogen, methyl or ethyl.

Compounds which are preferred among the Group D compounds, designated "Group E", are those compounds of Group D wherein $R^1$ is phenoxymethylene.

Compounds which are preferred among the Group E compounds, designated "Group F", are those compounds of Group E wherein $R^3$ is methyl.

Compounds which are preferred among the Group F compounds, designated "Group G", are those compounds of Group F wherein $R^5$ is hydrogen or methyl.

A most preferred compound is the compound of the following formula

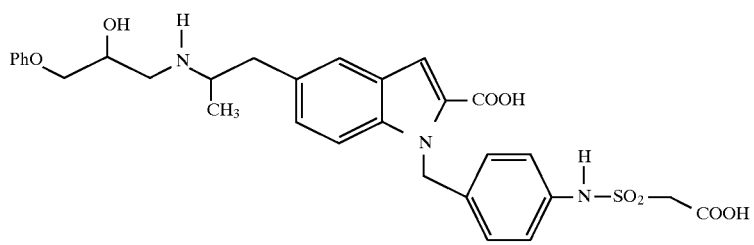

or a prodrug thereof, or a pharmaceutically acceptable salt of said compound or prodrug, effective in treating such condition, disease, or disorder, and a pharmaceutically acceptable carrier. Specific conditions, diseases, and/or disorders which are treatable with such compositions include diabetes, hyperglycemia, obesity, intestinal motility disorders, airway inflammatory disorders, depression, prostate disease, and dyslipidemia.

This invention also relates to a method of selectively activating a $\beta_3$-adrenergic receptor in humans or an animal, comprising administering to said human or animal in need of such activation an effective amount of a compound of formula (I) as defined hereinabove. A preferred method of the foregoing method is that the animal to which a compound of formula (I) is administered to is a dog.

Preferred compounds, designated "Group A", are those compounds of formula I, as defined hereinabove, wherein $R^1$ is phenoxyalkyl having 1 to 4 carbons in the alkyl portion where the optional substituents are as defined hereinabove and $R^2$, $R^3$, $R^4$ and $R^5$ are as defined hereinabove.

Compounds which are preferred among the Group A compounds, designated "Group B", are those compounds of Group A wherein $R^2$ is hydrogen.

Another most preferred compound is the compound of the following

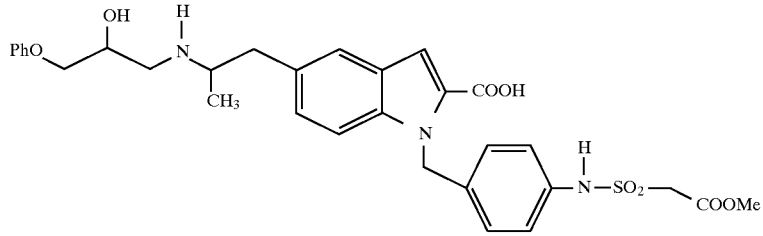

Salt forms of the above compounds are also preferred.

This invention also relates to a method of treating a condition selected from the group consisting of diabetes, hyperglycemia and obesity in a mammal, comprising administering to a mammal in need of such treatment an effective amount of a compound of formula I, or a prodrug thereof, or a pharmaceutically acceptable salt of said compound or prodrug.

This invention also relates to compositions useful for increasing the content of lean meat in animals, comprising an amount of a compound of formula I, or a prodrug thereof, or a pharmaceutically acceptable salt of said compound or prodrug, effective in increasing said lean meat content, and a pharmaceutically acceptable carrier.

This invention also relates to a feed premix comprising a compound of formula I, or a prodrug thereof, or a pharmaceutically acceptable salt of said compound or prodrug and one or more carriers.

This invention further provides a high potency concentrate comprising a compound of formula I, or a prodrug thereof, or a pharmaceutically acceptable salt of said compound or prodrug and one or more carriers.

This invention also relates to a method of increasing the content of lean meat in animals comprising administering to an animal an effective amount of a compound of formula I, or a prodrug thereof, or a pharmaceutically acceptable salt of said compound or prodrug.

This invention also relates to a method for treating prostate disease in a mammal, preferably a human, comprising administering to a mammal in need of such treatment an effective amount of a compound of formula I, or a prodrug thereof, or a pharmaceutically acceptable salt of said compound or prodrug.

The present invention also relates to a method of treating a condition selected from the group consisting of intestinal motility disorders such as irritable bowel syndrome, peptic ulceration, esophagitis, gastritis and duodenitis, (including that induced by H. pylori), intestinal ulcerations (including inflammatory bowel disease, ulcerative colitis, Crohn's disease and proctitis) and gastrointestinal ulcerations in a mammal, preferably a human, comprising administering to a mammal in need of such treatment an effective amount of a compound of formula I, or a prodrug thereof, or a pharmaceutically acceptable salt of said compound or prodrug.

The present invention also relates to a method for treating depression in a mammal, preferably a human, comprising administering to a mammal in need of such treatment an effective amount of a compound of formula I, or a prodrug thereof, or a pharmaceutically acceptable salt of said compound or prodrug.

The present invention also relates to a method for treating dyslipidemia in a mammal, preferably a human, comprising administering to a mammal in need of such treatment an effective amount of a compound of formula I, or a prodrug thereof, or a pharmaceutically acceptable salt of said compound or prodrug.

The present invention also relates to a method of treating airway inflammatory disorders, especially asthma, comprising administering to a mammal in need of such treatment an effective amount of a compound of formula I, or a prodrug thereof, or a pharmaceutically acceptable salt of said compound or prodrug.

This invention includes prodrugs of compounds of formula I having free amino, amido, hydroxy or carboxylic groups. Prodrugs are understood to comprise an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and are selected from 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs are also understood to include carbonates, carbamates, amides and alkyl esters which are covalently bonded to the above substituents of formula I through the carbonyl carbon prodrug side chain. Prodrugs also include compounds in which the secondary amine and its β-hydroxy when taken together form a group of the formula

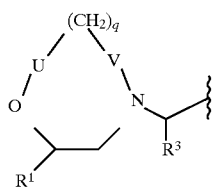

wherein $R^1$ and $R^3$ are as defined in formula I, q is 0 or an integer from 1 to 6, and U and V are each independently carbonyl, methylene, $SO_2$ or $SO_3$, wherein methylene is optionally substituted with hydroxy.

It is noted that certain compounds of formula I, wherein the $R^4$ and $R^5$ moieties are either or both $(C_1$-$C_4)$alkyl and, therefore, is a carboxylic acid ester moiety, are both active compounds and prodrugs. That is, the esters just mentioned are active compounds. They can also hydrolyze in the body to yield the corresponding (free) carboxylic acids which are also themselves active compounds. Such hydrolysis can be desirable since the free acid is selective for the $β_3$-subtype adrenergic receptor. $β_3$-selectivity reduces or avoids undesirable effects that may be present with $β_1$- and/or $β_2$-agonism, such as increased heart rate, smooth muscle tremoring, and decreased blood pressure.

It will be appreciated by those skilled in the art that compounds of formula I contain at least one chiral center, and possibly two chiral centers when $R^3$ is not hydrogen. Accordingly, compounds of formula I may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of the diseases or conditions noted herein, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the said utilities by the standard tests described hereinafter.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo", as used herein, unless otherwise indicated, includes chloro, fluoro, bromo and iodo.

The term "treating" as used herein includes preventative as well as disease remitative treatment.

Particular values of $(C_1$-$C_6)$alkyl include methyl, ethyl, propyl, isopropyl, butyl, isobutyl, t-butyl, pentyl, isopentyl, and hexyl.

Particular values of $(C_1$-$C_6)$alkoxy or $(C_1$-$C_8)$alkoxy include methoxy, ethoxy, propoxy, isopropoxy, butoxy, isobutoxy, t-butoxy, pentoxy, isopentoxy, and hexoxy, heptoxy and octoxy.

Particular values of $(C_3$-$C_8)$cycloalkyl include cyclopropyl, cyclobutyl, cyclopentyl, cyclohexyl, and cycloheptyl.

More particular values of $(C_1$-$C_6)$alkyl include the values of $(C_1$-$C_3)$alkyl, including methyl, ethyl, propyl, and isopropyl.

More particular values of $(C_1$-$C_6)$alkoxy include the values of $(C_1$-$C_3)$alkoxy, including methoxy, ethoxy, propoxy, and isopropoxy.

DETAILED DESCRIPTION

The compounds of this invention are readily prepared according to the reaction sequence shown in Scheme I, hereinbelow.

The expression "reaction inert solvent" refers to any solvent which does not interact with starting materials, reagents, intermediates or products in a manner which adversely affects the reaction or yield of the desired product.

Step A: Benzylation

Benzylation of an indole of formula (i), where R is $R^4$ as defined above for compounds of formula (I) or a carboxylic acid protecting group, is effected with either 4-nitrobenzyl bromide or 4-nitrobenzyl chloride with sodium and ammonia, sodium or potassium hydride, or triethylamine in DMSO, DMF, toluene, benzene, or acetonitrile at about 0° to 100° C. with the preferred conditions being sodium hydride in DMSO.

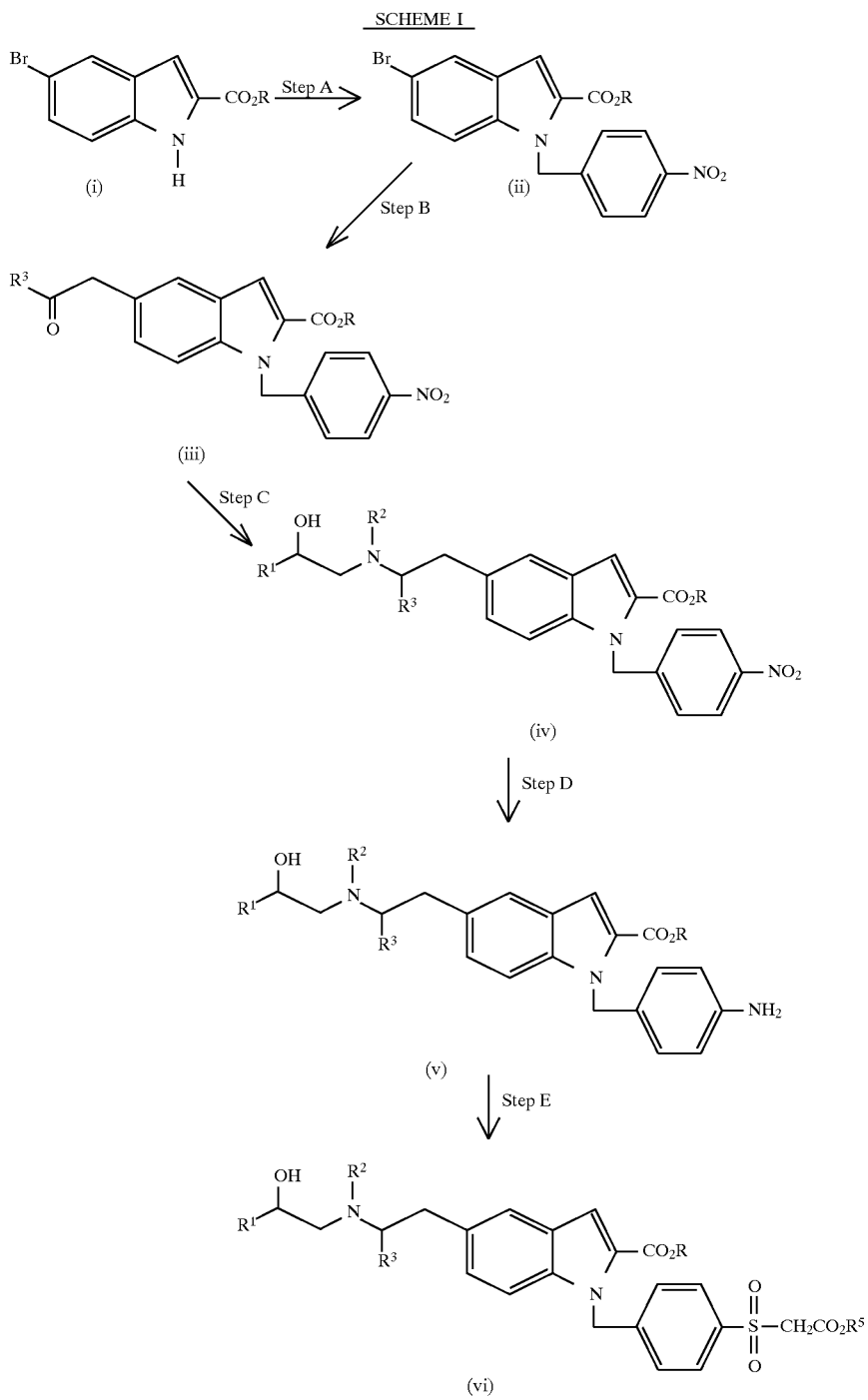

Step B: Reaction on Bromoindole

A bromoindole of formula (ii) is reacted with palladium. (II) acetate, tri-o-tolylphosphine, and $R^3COCH_2Sn(Bu)_3$, which is prepared in situ by the reaction of tributyl tin methoxide and $AcOC=CH_2R^3$ (e.g., $R^3=Me$, isopropenylacetate) in a non-polar solvent such as toluene, benzene, or hexane at about 10° to 150° C. Preferably the reaction is done in toluene at about 95° C.

Step C: Reductive amination

An aldehyde ($R^3=H$) or ketone ($R^3=(C_1-C_6)$alkyl) of the formula (iii) is coupled with an amine (primary if $R^2=H$, secondary if $R^2=(C_1-C_6)$alkyl) utilizing any of the following reducing conditions: sodium cyanoborohydride, sodium triacetoxyborohydride, sodium borohydride, hydrogen and a metal catalyst, zinc and hydrochloric acid, formic acid, or borane dimethylsulfide followed by treatment with formic acid. Solvents may be selected from alcohols, ethyl acetate, acetic acid, chlorinated hydrocarbons, or THF and the temperature is between about −60° C. to 50° C. Preferably the reaction is run in $CH_2Cl_2$, at room temperature, with acetic acid and sodium triacetoxyborohydride.

Step D: Reduction of $NO_2$

Reduction of a nitrobenzyl compound of the formula (iv) to a benzylamine of the formula (v) is conducted under a variety of reducing conditions including hydrogenation with palladium, platinum, or Raney nickel catalysts, transfer hydrogenations with reagents such as phenylhydrazine and dissolving metal reductions which will not affect other functional moieties such as the ester (lithium cobalt phthalocyanine or iron). These reductions are carried out in solvents such as benzene, toluene, dioxane, ethyl acetate, alcohols, DMF or THF. The preferred reduction conditions involve hydrogenation with 10% Pd/C in THF.

Step E: Sulfonylation

Sulfonylation of a benzylamine of the formula (v) is carried out with the appropriate sulfonyl chloride in the presence of amines such as triethylamine, Hunig's base, morpholine or pyridine in solvents such as chlorinated hydrocarbons, THF, toluene, or acetonitrile and the temperature is from about −78° C. to 50° C. Preferably the reaction is run in $CH_2Cl_2$, with triethylamine, starting at about −78° C. and then warmed to ambient temperature.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid—liquid) extraction techniques.

Certain of the compounds of formula I, for example those which have free carboxylic acid functionality, form pharmaceutically-acceptable cation salts by reacting the free acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amino acid prodrugs of this invention may be prepared by conventional peptide coupling reactions coupling a free amino or carboxylic group of the compound of formula I with an amino acid or a polypeptide, e.g. dipeptide, chain. The coupling reaction is generally conducted at a temperature of about −30° to about 80° C., preferably about 0° to about 25° C. Suitable coupling reagents are usually present, such as dicyclohexylcarbodiimide with hydroxybenzotriazole (HBT), N-3-dimethyl-aminopropyl-N'-ethylcarbodiimide with HBT, 2-ethoxy-1-ethoxycarbonyl-1, 2-dihydroquinoline, carbonyl diimidazole with HBT, or diethylphosphoryl-cyanide. The reaction is generally conducted in an inert solvent such as acetonitrile, methylene chloride, chloroform, dimethylformamide, dioxane, tetrahydrofuran, dimethoxyethane, or water, or a mixture of two or more such solvents.

Ester, carbonate and carbamate prodrugs of this invention may be prepared by reaction of a free hydroxyl or amino group of the compound of formula I with an activated carbonyl containing molecule such as acetyl chloride or ethyl chloroformate. The reaction can be carried out neat or in the presence of a reaction inert solvent such as methylene chloride, at a temperature from about −78° to about 100° C. Alcohols can also be reacted with cyanogen chloride in the presence of a Lewis acid to form carbamates.

Prodrugs in which the secondary amine and its β-hydroxy, taken together, form a group of the formula

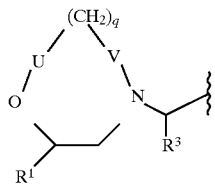

are formed by methods analogous to those described in U.S. Pat. No. 4,593,023, European Patent Application 170,135A published on Jul. 21, 1984 and U.S. Pat. No. 4,607,033.

When treating any of the conditions, disorders and/or diseases previously disclosed herein, generally satisfactory results are obtained when the compounds of the formula I, prodrugs, or pharmaceutically acceptable salts thereof (hereinafter also referred to as "active ingredients" or "active compounds") are administered to mammals, including humans, via either the oral or the parenteral route. Administration by the oral route is preferred in humans and animals, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 20 mg/kg body weight of the subject per day, preferably about 0.1 to about 10 mg/kg body weight per day, administered singly or as a divided dose. However, the optimum dosage for the individual subject being treated will be determined by the person responsible for the treatment, generally smaller doses being administered initially and thereafter increasing increments made to determine the most suitable dosage. This will vary according to the particular compound employed and with the subject being treated.

The compounds of the present invention can be used in combination with a pharmaceutically acceptable carrier or diluent as a pharmaceutical composition. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally, for example, intramuscularly, intravenously or subcutaneously. For parenteral administration the compounds can be combined with sterile aqueous or organic media to form injectable solutions or suspensions or a sterile aqueous solution which may contain other substances, for example, enough salts or glucose to make the solution isotonic. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in humans and companion animals.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The effective dosage of the active ingredient employed may vary depending on the particular compound employed, the mode of administration, the condition being treated and the severity of the condition being treated.

As a consequence of their action in reducing body fat (lipolysis), the compounds of the present invention possess utility for increasing lean meat deposition and/or improving the lean meat to fat ratio in animals, including poultry and ungulate animals such as swine, cattle, sheep, and goats. Compounds of formula I can additionally be used for the treatment of obese household pets, for example companion animals such as dogs and cats, with the treatment of dogs being especially preferred. The administration of a compound of formula I can be effected orally or parenterally. An amount of a compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active ingredient can also be added directly to the feed, as such, or in the form of an animal feed supplement, also referred to as a premix or concentrate. A premix or concentrate of a therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active compound in the concentrate are capable of wide variation since the amount of active compound in the finished feed may be adjusted by blending the appropriate proportion of premix with the feed to obtain a desired level of active compound.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of an active compound according to the invention. The mixtures are thoroughly blended by standard procedures, such as in a twin shell blender, to ensure homogeneity.

If the supplement is used as a top dressing for the feed, it likewise helps to ensure uniformity of distribution of the active compound across the top of the dressed feed.

For companion animals an active compound can be mixed with its food or put into a pet food treat.

Medicated drinking water and feed effective for increasing lean meat deposition and for improving lean meat to fat ratio are generally prepared by mixing a compound of the invention with a sufficient amount of animal feed or water to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred poultry and domestic pet feeds usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which the increase in lean meat deposition and improvement in lean mean to fat ratio is sought.

In general, parenteral administration involves injection of a sufficient amount of a compound of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

Paste formulations can be prepared by dispersing a compound of the present invention in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper level of active compound in the animal's body.

The present invention has several advantageous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

The compounds of this invention may be tested for hypoglycemic activity according to the following procedure and as an aid in determining dosages when compared to other compounds and standards.

Five to eight week old C57 BL/6J-ob/ob mice (obtained from Jackson Laboratory, Bar Harbor, Me.) are housed five per cage under standard animal care practices. After a one week acclimation period, the animals are weighed and 25 microliters of blood are collected via an ocular bleed prior to any treatment. The blood sample is immediately diluted 1:5 with saline containing 2% sodium heparin, and held on ice for glucose analysis. Animals are then regrouped, in groups of five per cage, such that the mean glucose values of the groups are similar, dosed daily for five days with test compound (0.01–20 mg/kg), a positive control such as englitazone or ciglitazone (50 mg/kg p.o.) (U.S. Pat. No. 4,467,902; Sohda et al., Chem. Pharm. Bull., vol. 32, pp. 4460–4465, 1984), or vehicle. All compounds are administered by oral gavage in a vehicle consisting of 0.25% w/v methyl cellulose. On day 5, the animals are weighed again and bled (via the ocular route) for blood glucose levels. The freshly collected samples are centrifuged for two minutes at 10,000×g at room temperature. The supernatant is analyzed for glucose, for example, with the ABA 200 Bichromatic Analyzer™ (a registered trademark of Abbott Laboratories, Diagnostics Division, 820 Mission Street, So. Pasadena, Calif. 91030), using the A-gent™ glucose UV reagent system (hexokinase method) (a modification of the method of Richterrich and Dauwalder, Schweizerische Medizinische Wochenschrift, 101, 860 (1971)), using 20, 60 and 100 mg/dl standards. Plasma glucose is then calculated by the equation:

$$\text{Plasma glucose (mg/dl)} = \text{Sample value} \times 5 \times 1.67 = 8.35 \times \text{Sample value}$$

where 5 is the dilution factor and 1.67 is the plasma hematocrit adjustment (assuming the hematocrit is 40%).

The animals dosed with vehicle maintain substantially unchanged hyperglycemic glucose levels (e.g., 250 mg/dl), while positive control animals have depressed glucose levels (e.g., 130 mg/dl). The glucose lowering activity of test compounds is expressed in terms of % glucose normalization. For example, a glucose level which is the same as the positive control is expressed as 100%.

Selectivity of a compound for $\beta_3$-receptors over $\beta_2$- and $\beta_1$-receptors may be determined using the following procedures.

In vitro selectivity may be determined by measurement of cyclic adenosine mono-phosphate (cAMP) accumulation in Chinese hamster ovary cells. Chinese hamster ovary cells uniquely transfected with the gene for the human $\beta_1$-, $\beta_2$- or $\beta_3$-receptor (Granneman, Mol. Pharmacol., 1991, 40, pp. 895–899) are grown to confluence in Ham's F12 media (Gibco BRL, Life Technologies, Inc., Grand Island, N.Y.) containing 10% fetal bovine serum, 500 mg/ml Geneticin, 100 U/ml penicillin, 100 mg/ml streptomycin and 250 ng/ml fungizone according to the procedure described in American Type Culture Collection Catalogue of Cell Lines and Hybridomas, Seventh Edition, 1992, p. 36, ATCC CCL 61 CHO-K1. Compounds are prepared as 10 mM stock solutions in DMSO (0.1% DMSO, final concentration), diluted in Ham's F12 media and added to the cells at $10^{-10}$ to $10^{-5}$M along with $10^{-3}$M isobutylmethylxanthine to inhibit phosphodiesterase activity. The media and cells are then incubated for 5 minutes at 37° C. At the end of this period, the media is aspirated and the cells lysed in 0.01N HCl. The cellular content of cAMP can then be determined by radioimmunoassay (RIA) using a kit from New England Nuclear (Burlington, Mass.). There is a direct correlation between the cellular content of cAMP and the agonism of the $\beta_1$-, $\beta_2$-, or $\beta_3$-receptor. The non-selective adrenergic agonist, norepinephrine, is included as a positive control at $10^{-5}$M. Data are expressed as fold increase over basal.

In vitro activity of compounds of formula I for $\beta_3$-agonist selectivity and lipolysis in dogs can be determined according to the following procedures. References: Taouis, M.; Berlan, M.; Montastruc, P.; Lafontan, M. J. Pharmacol. Exp. Ther. 1987, 242, 1041–1049. Taouis, M.; Valet, P.; Estan, L.; Lafontan, M.; Montastruc, P.; Berlan, M. J. Pharmacol. Exp. Ther. 1989, 250, 1061–1066. Galitzky, J.; Reverte, M.; Portillo, M.; Carpene, C.; Lafontan, M.; Berlan, M. Am. J. Physiol. 1993, 264, E403–E412.

Isolation of dog fat cells

A biopsy of adipose tissue (generally omental adipose tissue) is performed in anesthetized dogs. Then, the tissue is cut into small pieces and transferred into plastic vials containing the incubation buffer (Krebs-Ringer bicarbonate (KRBA) buffer, pH 7.4) with glucose (1 mg/100 ml) and albumin (40 mg/ml), supplemented with crude collagenase (0.5 mg/ml). The tissue is incubated from 40 to 50 min. at about 37° C. in a shaking water bath (60–80 strokes per min.). The fat cells are separated from the stroma by filtration over a nylon filter. The filter is rinsed with one volume of collagenase-free albumin buffer. The cells are washed three to four times with the KRBA buffer using the same procedure for their separation. After the final wash, they are ready to be used for the lipolytic assay.

In Vitro Assay for the Lipolytic Effect of $\beta_3$-Agonists on Canine Fat Cells KRBA is used for the lipolysis experiments, however, most physiological buffers can be substituted. It is necessary to supplement the buffer with albumin in order to prevent intracellular accumulation of free fatty acids which could inhibit lipolysis. The most commonly used albumin preparation is bovine serum albumin, fraction V (Sigma). The rate of glycerol release is almost linear between 10 and 200 min. with or without agents that stimulate or inhibit lipolysis.

The stock solution of fat cells obtained after isolation is diluted and distributed in plastic tubes (500 ml aliquots with 10–15 mg of total fat cell lipid). Pharmacological agents—agonists and/or antagonists—are added, in small volumes (10 ml), at the suitable concentrations ($10^{-10}$ to $10^{-4}$M) (obtained by dilution of concentrated stock solutions). The tubes are maintained at about 37° C. in a shaking water bath for about 1 hour, and then lipolysis is stopped by putting the plastic tubes on ice.

Glycerol release is used for the calculation of the rate of lipolysis. It is a valid index only if hydrolysis of fat cell triacylglycerol is complete. Glycerol is not reutilized by fat cells to any extent, probably because glycerol kinase activity is negligible in adipose tissue. Glycerol is measured directly in the incubation medium.

Glycerol is measured in 50 to 200 ml aliquots of incubation medium using an enzymatic (Wieland, O. H., in *Methods of Enzymatic Analysis*, Bergmeyer, H. U., Ed., Vol VI, 1984, pp 504–510, Verlag Chemie, Weinheim) or a radiometric technique (Bradley, D. C. and Kaslow, H. R., *Anal. Biochem.*, 1989, 180:11–16). The lipid content of the incubation vials is determined gravimetrically. Results are expressed as mmol of glycerol released per 100 mg total fat cell lipid per hour.

In vivo efficacy may be determined by measurement of oxygen consumption and ambulatory activity on male Sprague-Dawley rats (Charles River, Wilmington, Mass.). Whole animal oxygen consumption may be measured using an open circuit, indirect calorimeter (Oxymax™, from Columbus Instruments, Columbus, Ohio). The Oxymax gas sensors are calibrated with nitrogen ($N_2$) gas and gas mixture (0.5% carbon dioxide, 20.5% oxygen, 79% nitrogen; ABCO Industrial Supplies, Waterford, Conn.) before each experiment. Rats (male, Sprague Dawley, 300–380 g body weight) are placed in sealed chambers (43×43×10 cm) of the calorimeter and the chambers placed in activity monitors. Air flow rate through the chambers is set at 1.6–1.7 l/min. The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis; ambulatory activity is recorded when two consecutive beams are broken (repeated interruptions of the same beam are not registered) and the results are recorded as counts.

Basal oxygen consumption and ambulatory activity can be measured every 10 minutes for 2.5 to 3 hours. At the end of the basal period, the chambers are opened and the test compound (0.01 to 20 mg/kg, prepared in water or other suitable vehicle) or an equivalent volume of vehicle is administered by oral gavage. Oxygen consumption and ambulatory activity can be measured every 10 minutes for an additional three hours post-dosing. Percent change in oxygen consumption may be calculated by averaging the post-dosing values for 2.5 hours and dividing by basal oxygen consumption (average of the predosing values except the first hour). Oxygen consumption values obtained during time periods where ambulatory activity exceeds 100 counts are excluded from the calculation. Thus, the values represent % change in resting oxygen consumption.

In vivo selectivity for $\beta_1$- and $\beta_2$-adrenergic receptors may be determined by measurements of heart rate, blood pressure and plasma potassium concentration gathered on conscious catheterized rats (male, Sprague Dawley, 300–380 g body weight). To implant catheters, rats are anesthetized with pentobarbital (50–60 mg/kg, i.p.) and the left carotid artery is cannulated with PE50 tubing. The catheter is tunneled subcutaneously, exteriorized at the back of the neck, filled with a solution of polyvinylpyrrolidone in heparinized saline, flame-sealed and taped. Experiments are performed 7 days after surgery. On the day of the experiment, the catheters are untaped and flushed with saline. After at least 30 minutes, basal values for heart rate and blood pressure are measured by attaching the catheter to a pressure transducer, the results recorded on a Grass Model 7 polygraph (Grass Medical Instruments, Quincy, Mass.), and a basal blood sample (0.5 ml) is obtained from the arterial catheter. After obtaining basal values, the test compound or vehicle is administered by oral gavage, and blood pressure (measure of $\beta_2$ activity) and heart rate (measure of $\beta_1$ activity) measurements are taken at 15, 30, 45 and 60 minutes and blood samples for potassium determination ($\beta_2$) are obtained at 30 and 60 min. Isoproternol, a non-selective $\beta$-agonist can be tested as a positive control at doses ranging from 0.001 to 1 mg/kg (injected s.c. in saline vehicle).

Plasma potassium is determined by flame spectrophotometry. To determine changes, basal values are subtracted from the average of the post dosing values.

Compounds of the formula I also have the effect of reducing intestinal motility and thus find utility as aiding in the treatment of various gastrointestinal disorders such as irritable bowel syndrome, peptic ulceration, esophagitis, gastritis and duodenitis, (including that induced by *H. pylori*), intestinal ulcerations (including inflammatory bowel disease, ulcerative colitis, Crohn's disease and proctitis) and gastrointestinal ulcerations. It has been proposed that the motility of non-sphincteric smooth muscle contraction is mediated by activity at $\beta_3$-adrenergic receptors. The availability of a $\beta_3$ specific agonist, with little activity at $\beta_1$- and $\beta_2$-receptors will assist in the pharmacologic control of intestinal motility without concurrent cardiovascular effects.

In vivo activity of the compounds of formula I for the treatment or prevention of intestinal motility disorders can be determined according to the following procedures. Eighteen-hour fasted male Sprague Dawley derived (CD) rats (175–225 grams) are dosed with 0.01–20 mg/kg p.o. of compound or vehicle (distilled water). Thirty minutes after administration of compound, the rats are orally dosed with 0.25 ml of a solution of sodium chromate in 0.9% saline containing about 20,000 cpm of $^{51}Cr$ (specific activity 350 mCi/mg Cr). Twenty minutes later, the rats are sacrificed, the gastroesophageal, pyloric, and ileocecal junctions are then ligated, and the stomachs and small intestines removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}$Cr in each segment times the segment number: geometric center=S ((fraction of $^{51}$Cr per segment)×(segment number)). For these calculations the stomach may be considered segment number 0, and the ten intestinal segments as numbers 1 to 10. Thus, a geometric center of 0.0 would indicate that the entire load of $^{51}$Cr had remained in the stomach. Data from two experiments may be pooled, and statistical evaluations can be made using Dunnett's multiple comparison test.

Alternatively, in groups of 8, overnight-fasted male Sprague-Dawley (CD) rats (175–225 grams) may be anesthetized with methoxyflurane. A small abdominal incision is then made, and the pylorus ligated. Immediately after the ligation, a solution of compound or the vehicle (distilled water) is injected into the proximal duodenum. The doses of compound used should be 0.01–20 mg/kg. The incisions can then be closed and the rats can be allowed to recover from the anesthesia. Two hours after the ligation the rats are sacrificed and the gastric fluid collected and cleared by centrifugation. Total volume of secretion can be determined by weight, and acidity can be determined by titration to pH 7.0 with 0.1N NaOH using an automatic titrator (Radiometer TTT85). The data from two experiments are then pooled. A group of rats treated with 10 mg/kg of the antisecretory histamine $H_2$-receptor antagonist cimetidine may be included in each experiment as a positive control. Statistical evaluations can be made using Student's t-test.

In vitro activity for relaxation of contracted ileum from isolated guinea pig ileum can be determined according to the following procedure. Fresh isolated segments of guinea pig ileum (about 1.5 cm long) are mounted in tissue baths containing Tyrode's physiological salt solution at about 30° C. and aerated continuously with $O_2$:$CO_2$ (95%:5%). Tissues are then equilibrated for 60–90 minutes under 4.0 gm tension in order to achieve stable baselines. Histamine is then added to the baths in a cumulative fashion in concentrations ranging from 1 nM to 10 mM. The maximum tension generated after each addition of histamine is recorded on a Grass Physiograph (Grass Medical Instruments, Quincy, Mass.). The tissues are then washed with several changes of Tyrode's solution, basal tension can be readjusted to 4.0 grams, and a stable baseline is then again obtained. Each tissue may then be exposed to a single concentration of a compound (range 1 nM to 10 mM) or vehicle and after a 30 minute equilibration period, the histamine dose response curve may then be repeated. Results from multiple experiments are standardized (0–100%) to the maximum response of the control tissues and plotted as percent maximum tension versus the log of the histamine concentration in the absence and presence of the compound.

Compounds of formula I can be assessed for antidepressant activity in vivo according to the following procedure.

Male CD1 mice weighing between 20 and 25 g, and Sprague-Dawley rats weighing between 200 and 250 g, may be obtained from Charles River (Wilmington, Mass.). Compounds of formula I are dissolved in water. The compounds may be administered to mice in a volume of 10 ml kg$^{-1}$, and to rats in a volume 2 ml kg$^{-1}$. Control animals receive the vehicle. Positive test results for the following parameters indicate antidepressant activity.

I. Antagonism of hypothermia induced by reserpine

Mice are given reserpine (2.5 mg kg$^{-1}$ i.p. dissolved in 1% citric acid). Their rectal temperatures may be measured 3.5 h later. The mice may then be divided into different groups so as to obtain the same mean rectal temperature in each group. Half an hour later (i.e., 4 h after reserpine), the mice are given the vehicle or compound. Rectal temperature can be measured again 90 min later (i.e., 5 hours and 30 min after the injection of reserpine) (Bourin et al., *The Value of the Reserpine Test in Psychopharmacology,* Arzneim. Forsch. 33, 1173, (1983)).

II. Antagonism of hypothermia induced by apomorphine

Half an hour after the mice are placed in individual cages, their rectal temperatures are recorded. The animals should be allocated so as to obtain the same mean rectal temperature in each group. Apomorphine (16 mg kg$^{-1}$ s.c.) can be given 30 min after the compound or its vehicle. Rectal temperature can be measured again 30 min after the apomorphine treatment (Puech et al, *Antagonism of Hypothermia And Behavioral Response To Apomorphine; A Simple, Rapid And Discriminating Test For Screening Antidepressants And Neuroleptics,* Psychopharmacology 75, 84, (1981)).

III. Effect on learned helplessness behavior

This test is performed basically as described by Giral et al. *Reversal Of Helpless Behavior In Rats By Putative 5-HT$_{IA}$ Agonists.* Biol. Psychiat. 23, 237. (1988). Electric footshocks are delivered to male albino Sprague-Dawley rats placed in chambers (20×10×10 cm) with Plexiglass® walls and covers. The floors are made of stainless-steel grids (1.5 cm mesh). A constant-current shock is delivered as 60 scrambled, randomized inescapable shocks (15 s duration, 0.8 mA, every 60+15 s) to the grid floor. Control rats are then placed in identical chambers for 1 h but no shock is administered. All preconditioning trials are performed on day 1 between 9 a.m. and 11 a.m. Avoidance training is initiated 48 h (day 3) after inescapable shock in automated two-way shuttle-boxes (60×21×30 cm) with Plexiglass® walls and a floor consisting of stainless-steel rods spaced 1.0 cm apart in order to evaluate escape deficits. Each shuttlebox is divided into two chambers of equal size by a stainless-steel partition, with a gate providing access to the adjacent compartment through a 7 cm×7 cm space. Shuttlebox sessions are performed for 3 consecutive days (days 3, 4 and 5). The animals are placed individually in the shuttlebox and allowed to habituate to the environment for 5 min (for the first session only) and then subjected to 30 trials. The intertrial interval should be 30 seconds. A light signal, used as a conditioned stimulus, is presented during the first 3 seconds of each trial. Crossing the gate into the other compartment of the box during this 'conditioned-stimulus only' period (referred to as avoidance response) allows the rats to avoid shocks. A period with conditioned stimulus plus electric foot-shock (0.8 mA) may be presented if an avoidance response does not occur. Crossing the gate into the other compartment during this conditioned stimulus plus shock period is referred to as an escape response. Absence of escape response during the 3-second duration conditioned stimulus plus shock should be considered to be an escape failure.

The rats (n=10 per group) should be treated randomly according to one of the following protocols: the control sample, which receives no shock, and is given vehicle; experimental animals with inescapable shock are treated daily with vehicle or compound. Animals should be treated orally over 5 consecutive days, i.e. 6 hours after shock pretreatment on day 1, and then twice per day, a half dose in the morning (30 min before shuttle-box session) and a half dose in the afternoon (except on the 5th day). Statistical analysis can be performed on the mean number of escape failures using a two-way analysis of variance (subjects X sessions) followed by Dunneft's test.

Compounds of formula I also have the effect of bronchial relaxation and increased ciliary motility and thus may be useful in the treatment of airway inflammatory disorders such as asthma and obstructive lung disease. In vitro activity of compounds for the treatment of airway inflammatory disorders can be determined by measurement of guinea-pig bronchial ring relaxation according to the following procedure.

Guinea-pig main bronchial rings are obtained from tri-colored guinea-pigs of either sex (250–350 g) anesthetized with urethane (1.25 g $kg^{-1}$, i.p.) and are suspended under an initial tension of 2.0 g in Krebs solution at 37° C. gassed with 95% $O_2$:5% $CO_2$. After about 1 hour of equilibration, guinea-pig bronchial rings are contracted with acetylcholine ($10^{-3}$M) and relaxed to maximal relaxation with theophylline ($3\times10^{-3}$M), then allowed to equilibrate for a further 60 min while they are washed with Krebs solution every 15 min.

Changes in tension are measured isometrically with strain gauges and amplifiers and displayed on a recorder. The composition of the Krebs solution is (mM): NaCl 118.0, KCl 5.4, $CaCl_2$ 2.5, $KH_2PO_4$ 1.2, $MgSO_4$ 1.2, $NaHCO_3$ 25.0 and glucose 11.7.

To test effects of compounds on resting tension, cumulative concentration-response curves are obtained by addition of the test compounds ($10^{-9}$ to $10^{-6}$M) every 10–20 min until a plateau is reached. The relaxant effects of the compounds are expressed as percentages of the maximal relaxation induced by theophylline ($3\times10^{-3}$M).

In vitro activity of the compounds of formula I for prostate disease can be determined according to the following procedures.

Ventral prostates of male Sprague-Dawley rats (300–400 g) anesthetized with diethyl ether are quickly excised and placed in oxygenated Krebs solution. While maintained at room temperature in this buffer, adherent fatty and connective tissues are removed. The prostates are then suspended in 10-ml organ baths containing Krebs solution warmed to 37° C. and aerated with a mixture of 95% $O_2$ and 5% $CO_2$. The composition of the Krebs solution is 118.4 mM NaCl, 4.7 mM KCl, 1.2 mM $MgSO_4$, 2.5 mM $CaCl_2$, 11.1 mM dextrose, 25.0 mM $NaHCO_3$ and 1.2 mM $KH_2PO_4$, dissolved in distilled and demineralized water. The tissues are attached to isometric force-displacement transducers and isometric contraction is recorded under a loading tension of 0.5 g. Equilibration is undertaken for 1 to 2 hr before the addition of test compounds. Submaximal contractions are first elicited by repeated concentrations of $1\times10^{-6}$M phenylephrine until constant responses are obtained. The control and test compound-treated experiments are done in different preparations. A concentration-response curve to cumulate concentrations of phenylephrine or acetylcholine ($10^{-9}$ to $10^{-4}$M) is determined. For testing compounds, a concentration response curve to phenylephrine or acetylcholine is determined in the presence of the compounds (1 or 10 $\mu$M).

In vitro activity of compounds of formula I can also be determined for specific efficacy in human prostate as follows.

Prostatic tissue specimens are obtained from patients with symptomatic BPH, who are undergoing open prostatectomy. Isolated human prostatic tissue is cut into five to eight strips (3 mm wide, 3 mm thick and 15 mm long in each strip). The strips are mounted vertically in organ baths containing 20 ml Krebs-Henseleit solution of the following composition (mM): NaCl 112, KCl 5.9, $MgCl_2$ 1.2, $CaCl_2$ 2, $NaHCO_3$ 25, $NaHPO_4$ 1.2, glucose 11.5. The medium is maintained at 37° C. and at pH 7.4, and is equilibrated with a gas mixture consisting of 95% $O_2$ and 5% $CO_2$. A resting tension of 0.5 g is applied and the responses are recorded isometrically through a force-displacement transducer. The preparations are equilibrated for 90 min before starting the experiments.

Concentration-response curves for phenylephrine or acetylcholine ($10^{-9}$ to $10^{-4}$M) are determined by adding the compound directly to the bathing media in a cumulative fashion. For testing compounds, the prostate strips are incubated in the presence of compound (1 or 10 $\mu$M) for 30 minutes before and then phenylephrine or acetylcholine are added to the medium in a cumulative fashion to obtain to the concentration-response curve in the presence of the compound.

Compounds of the formula I lower triglyceride levels and cholesterol levels and raise high density lipoprotein levels and are therefore of use in combating medical conditions wherein such lowering (and raising) is thought to be beneficial. Thus, the compounds of formula I can be used in the treatment of hypertriglyceridaemia, hypercholesterolemia and conditions of low HDL (high density lipoprotein) levels in addition to the treatment of atherosclerotic disease such as of coronary, cerebrovascular and peripheral arteries, cardiovascular disease and related conditions.

The compounds may also be combined with other active ingredients known for use in the treatment of atherosclerosis and related conditions, for example fibrates such as clofibrate, bezafibrate and gemfibrozil; inhibitors of cholesterol biosynthesis such as HMG-COA reductase inhibitors, for example lovastatin, simvastatin and pravastatin; inhibitors of cholesterol absorption, for example beta-sitosterol and acyl CoA; cholesterol acyltransferase inhibitors, for example melinamide; anion exchange resins for example cholestyramine, colestipol or dialkylaminoalkyl derivatives of a cross-linked dextran; nicotinyl alcohol, nicotinic acid or a salt thereof; vitamin E; and thyromimetics.

Activity of compounds of formula I for dyslipidemia can be determined according to the following procedure. C57BL/6J ob/ob mice (male, 30–40 g body weight, Jackson Lab, Bar Harbor, Me.), housed 5 mice per cage in an environmentally controlled room, can be dosed once daily for 3 weeks with compound (0.01–20 mg/kg, n=15 per group) or vehicle (saline) by oral gavage. Body weight of each mouse can be measured daily and food intake per cage is determined by weighing the amount of food left in the trough. At the end of the study, 24 h after giving the final dose of compound, the mice may be sacrificed by decapitation and blood collected. Plasma concentrations of glucose, free fatty acids and triglyceride can be determined with the VP Super System Autoanalyzer (Abbott, Irving, Tex.).

Activity of compounds of formula I for decreasing body fat can be determined according to the following procedure. C57BU6J ob/ob mice (male, 30–40 g body weight, Jackson Lab, Bar Harbor, Me.) are housed 5 mice per cage in an environmentally controlled room with food (pelleted rodent chow) and water available ad libitum. The compounds or vehicle (water) can be dosed once daily for 3 weeks (0.01–20 mg/kg, n=15 per group) by oral gavage. Body weight of each mouse can be measured daily and food intake per cage determined by weighing the amount of food left in the trough. At the end of the study, 24 h after giving the final dose of compound, the mice are weighed and then sacrificed by cervical dislocation. The epididymal fat pads from each mouse are excised and weighed. The fat versus body weight ratio is determined for each mouse using the absolute body weights and the fat pad weights. A reduction in fat pad weight is indicative of a reduction in total body fat.

The compounds of formula I have gastro-intestinal protective effects and, therefore, are useful in the treatment and/or prevention of ulcers. Activity of compounds of formula I to protect against gastric ulcerations can be determined according to the following procedure.

Food (but not water) is withheld for 24 hours from female Sprague Dawley rats (Charles River, Wilmington, Mass.) weighing 70–120 g. Access to food is then allowed for 90 min. A single dose of β-adrenoceptor agonist (a compound of the present invention) is then administered p.o. (1 ml 100 $g^{-1}$) Indomethacin (Sigma Chemical Co., St. Louis, Mo.) (60 mg $kg^{-1}$, 1 ml 100 $g^{-1}$ body weight) is then injected subcutaneously. Control rats receive the subcutaneous injection of indomethacin and oral administration of vehicle (0.5% methyl cellulose in distilled water) for the β-adrenoceptor agonist. The animals are then allowed continued access to food but water is withdrawn. The animals are sacrificed by cervical dislocation 6 hours after dosing with indomethacin. The stomachs are removed, opened along the greater curvature and washed in 0.9% saline. An assessment of gastric damage is carried out by an observer who is unaware of the dosing regimen. A transparent plastic grid divided into 1 $mm^2$ sections is placed over the antrum and the area of macroscopic damage assessed as the total area of visible lesions in $mm^2$. This value is then expressed as a percentage of the total antral area.

The present invention is illustrated by the following Examples. However, it should be understood that the invention is not limited to the specific details of these examples.

EXAMPLE 1

1-(4-Carboxymethanesulfonylamino-benzyl)-5-[2-(2-hydroxy-3-phenoxypropylamino)-propyl]-1H-indole-2-carboxylic Acid To a solution of 5-[2-(2S-hydroxy-3-phenoxy-propylamino)-propyl]-1-[4-(2,2,2-trifluoro-ethanesulfonylamino)-benzyl]-1H-indole-2-carboxylic acid ethyl ester (277 mg, 0.428 mmol) in methanol (4 ml) was added 3N potassium hydroxide (1.5 ml, 4.5 mmol). The solution was warmed to about 60° C. for about 2 hours, cooled, and concentrated in vacuo to remove the methanol. Acetonitrile was added, and the solution was concentrated again. The pH of the aqueous solution was adjusted to 5.5 by careful addition of 1N hydrochloric acid. The precipitate was filtered, washed with water, and dried in air, then under vacuum, to give the title compound (185 mg).

The title compound can be purified by reverse phase HPLC. A Prodigy 50×250 mm 10 um C-18 (Phenomenex 2320 West 205th Street, Torrance, Calif. 90501) column is equilibrated to a steady baseline with 75% 0.1% TFA in distilled deionized water and 25% HPLC grade acetonitrile. The residue is dissolved in 20 ml of the mobile phase to which is added a few drops of TFA. The sample is injected onto the column and eluted with a gradient from 75 buffer:25 acetonitrile to 65 buffer:35 acetonitrile in 30 min. at 100 ml per min. The desired peak elutes in 20.5–25 min. These fractions are combined and concentrated to remove acetonitrile, and freeze-dried to give a white powder.

EXAMPLE 2

5-[2-(2-Hydroxy-3-phenoxy-propylamino)-propyl]-1-(4-methoxycarbonylmethanesulfonylamino-benzyl)-1H-indole-2-carboxylic Acid

2a. 5-Bromo-1-(4-nitro-benzyl)-1H-indole-2-carboxylic Acid

To a stirred solution of 5-bromo-1-(4-nitro-benzyl)-1H-indole-2-carboxylic acid ethyl ester (2.3 g, 5.7 mmol) in ethanol/water (2:1, 45 ml) at room temperature was added potassium hydroxide (0.96 g, 17.1 mmol). The solution was warmed to reflux for about 3 hours, cooled, and most of the ethanol was removed under reduced pressure. To the residue was added water, 0.5N sodium hydroxide and methylene chloride, and the two-phase mixture was suction filtered to remove some insoluble material. The aqueous layer was acidified to pH 2 with 6N hydrochloric acid, and the precipitate was filtered off, washed with water, and air dried to afford the title compound, (1.66 g).

2b. 5-Bromo-1-(4-nitro-benzyl)-1H-indole-2-carboxylic Acid Benzyl Ester

To a mixture of 5-bromo-1-(4-nitro-benzyl)-1-H-indole-2-carboxylic acid (1.66 g, 4.43 mmol) and sodium bicarbonate (0.93 g, 11.1 mmol) in dry dimethylformamide at room temperature under nitrogen was added benzyl bromide (2.275 g, 1.58 ml, 13.3 mmol). The reaction mixture was warmed to about 60° C. for about 16 hours and then the mixture was cooled, diluted with ethyl acetate, washed with dilute sodium bicarbonate solution and brine, dried over sodium sulfate, and concentrated in vacuo. The resulting residue was flash chromatographed on silica (60 g) with 20% ethyl acetate/hexanes. The purified product was taken up in hot toluene/heptane and allowed to crystallize slowly. The light brown solid was washed with heptane and dried in air, then under vacuum to give the title compound (1.73 g).

2c. 1-(4-Nitro-benzyl)-5-(2-oxo-propyl)-1H-indole-2-carboxylic Acid Benzyl Ester A solution of 5-bromo-1-(4-nitro-benzyl)-1H-indole-2-carboxylic acid benzyl ester (1.733 g, 3.72 mmol), tributyltin methoxide (1.79 g, 1.6 ml, 5.58 mmol), isopropenyl acetate (0.56 g, 0.61 ml, 5.58 mmol), palladium (II) acetate (41.5 mg, 0.19 mmol) and tri-o-tolylphosphine (113 mg, 0.37 mmol) in toluene (5 ml) was heated at about 95° C. under nitrogen for about 6 hours. The reaction solution was cooled, concentrated in vacuo, and subjected to flash chromatography on silica (105 g, 30% ethyl acetate/hexanes). The partially pure product was re-chromatographed on silica (12 g, 50% methylene chloride/hexanes) to give the title compound (547 mg).

2d. 5-[2-(2(S)-Hydroxy-3-phenoxy-propylamino)-propyl]-1-(4-nitrobenzyl)-1H-indole-2-carboxylic Acid Benzyl Ester To a solution of 1-(4-nitro-benzyl)-5-(2-oxo-propyl)-1H-indole-2-carboxylic acid benzyl ester (540 mg, 1.22 mmol) and 1-amino-3-phenoxypropan-2(S)-ol (245 mg, 1.46 mmol) in dichloroethane (20 ml) was added powdered sodium sulfate (1.73 g, 12.2 mmol), and the mixture was stirred for about one hour at room temperature under nitrogen. Acetic acid (87.9 mg, 0.084 ml, 1.46 mmol) and sodium triacetoxyborohydride (388 mg, 1.83 mmol) were added. After about 6 hours, additional sodium triacetoxyborohydride (194 mg, 0.915 mmol), acetic acid (0.2 ml, 3.5 mmol) and 1-amino-3-phenoxypropan-2(S)-ol (122 mg, 0.73 mmol) were added, and the mixture was stirred for about two days at room temperature under nitrogen. The reaction was then diluted with methylene chloride, washed with dilute sodium bicarbonate and brine, dried over sodium sulfate, filtered, and the solvent was removed in vacuo. The residue was flash chromatographed on silica (55 g), eluting with 5% methanol/methylene chloride, to give the title compound (500 mg) as a mixture of diastereomers.

2e. 5-{2-[tert-Butoxycarbonyl-(2(S)-hydroxy-3-phenoxy-propyl)-amino]-propyl}-1-(4-nitro-benzyl)-1H-indole-2-carboxylic Acid Benzyl Ester To a solution of benzyl 5-[2-(2(S)-hydroxy-3-phenoxypropylamino)-propyl]-1-(4-nitro-benzyl)-1H-indole-2-carboxylic acid benzyl ester (476 mg, 0.8 mmol) in methylene chloride (20 ml) stirring at room temperature under nitrogen was added di-tert-butyl dicarbonate (210 mg, 0.96 mmol). The reaction was stirred for about two days, the solvent was removed in vacuo, and the residue subjected to flash chromatography on silica (25 g, 22% ethyl acetate/hexanes) affording a total of 554 mg of the t-BOC-protected diastereomers (200 mg of each of the diastereomers was isolated cleanly, with the remainder of the material being a mixture of the diastereomers).

2f. 1-(4-Amino-benzyl)-5-{2-[tert-butoxycarbonyl-(2-hydroxy-3-phenoxypropyl)-amino]-propyl}-1H-indole-2-carboxylic Acid To a solution of 5-{2-[tert-butoxycarbonyl-(2(S)-hydroxy-3-phenoxypropyl)-amino]-propyl}-1-(4-nitro-benzyl)-1H-indole-2-carboxylic acid benzyl ester (134 mg, 0.19 mmol) in THF (6 ml) was added 14 mg of 10% Pd/C catalyst. The reaction mixture was hydrogenated on a Parr shaker at 45 psi for about 4 hrs and then filtered to remove the catalyst. The filtrate was concentrated under reduced pressure to afford a yellow foam (112 mg), AP-MS 572.

2g. 5-[2-(2-Hydroxy-3-phenoxy-propylamino)-propyl]-1-(4-methoxycarbonyl-methanesulfonylamino-benzyl)-1H-indole-2-carboxylic Acid To an about −78° C. solution of 1-(4-amino-benzyl)-5-{2-[tert-butoxycarbonyl-(2-hydroxy-3-phenoxy-propyl)-amino]-propyl}-1H-indole-2-carboxylic acid (110 mg, 0.19 mmol) in methylene chloride (12 ml) was added triethylamine (59 ml, 0.43 mmol) and chlorosulfonyl-acetic acid methyl ester (39.9 mg, 0.232 mmol). After stirring for about 15 mins and then allowing to warm to ambient temperature over about 1 hr the solution was partitioned between water and methylene chloride and then the organic layer was washed once with brine, dried over sodium sulfate, filtered, and then concentrated in vacuo to afford a foam (121 mg). This foam was redissolved in methylene chloride (7.5 ml) and cooled to about 0° C. before adding 2.5 ml of TFA (to generate a 25% TFA solution). The reaction mixture was stirred for about 1.5 h at room temperature, concentrated and azeotroped with heptane. The title compound can be purified by reverse phase HPLC using the conditions described in Example 1. AP-MS 608.

PREPARATION 1

5-Bromo-1-(4-nitro-benzyl)-1H-indole-2-carboxylic Acid Ethyl Ester

To a stirring solution of 5-bromo-1H-indole-2-carboxylic acid ethyl ester (2.68 g, 10 mmol, ICN) in dry dimethylsulfoxide (42 ml) at room temperature under nitrogen was added sodium hydride (264 mg, 11 mmol) as a slurry in hexane in four equal portions over about ten minutes. 4-Nitrobenzyl bromide (2.16 g, 10 mmol) in dry dimethylsulfoxide (12 ml) was added dropwise over about five minutes. The mixture was stirred 2 hours, poured into water (50 ml) and extracted with ethyl acetate. The solution was washed with brine, dried over sodium sulfate, filtered, and concentrated in vacuo. The residue was flash chromatographed on silica gel (110 g, methylene chloride) to give the title compound (3.28 g).

PREPARATION 2

1-(4-Nitro-benzyl)-5-(2-oxo-propyl)-1H-indole-2-carboxylic Acid Ethyl Ester A solution of 5-bromo-1-(4-nitro-benzyl)-1H-indole-2-carboxylic acid ethyl ester (3.28 g, 8.13 mmol), tributyltin methoxide (3.92 g, 3.51 ml, 12.2 mmol), isopropenyl acetate (1.22 g, 1.34 ml, 12.2 mmol), palladium (II) acetate (91 mg, 0.41 mmol) and tri-o-tolylphosphine (248 mg, 0.813 mmol) in toluene (10 ml) was heated at about 95° C. under nitrogen for about 3 hours. The reaction solution was cooled, concentrated in vacuo, and subjected to flash chromatography on silica (200 g, gradient from 10% ethyl acetate/hexane to 40% ethyl acetate/hexane), and then the partially pure product was recrystallized from toluene/heptane to give the title compound (1.91 g).

PREPARATION 3

5-(2-Methyl-[1,3]dioxolan-2-ylmethyl)-1-(4-nitro-benzyl)-1H-indole-2-carboxylic Acid Ethyl Ester A solution of 1-(4-nitro-benzyl)-5-(2-oxo-propyl)-1H-indole-2-carboxylic acid ethyl ester (1.91 g, 5.03 mmol), ethylene glycol (406 mg, 0.365 ml, 6.54 mmol), and p-toluenesulfonic acid monohydrate (110 mg, 0.58 mmol) in toluene (50 ml) was heated to about 150° C. under a Dean-Stark trap under nitrogen for two hours. The solution was cooled, diluted with ethyl acetate, washed with dilute sodium bicarbonate and brine, dried over sodium sulfate, filtered, and dried under reduced pressure to give the title compound in crude form (2.4 g), which was reacted without further purification.

PREPARATION 4

1-(4-Amino-benzyl)-5-(2-methyl-[1,3]dioxolan-2-ylmethyl)-1H-indole-2-carboxylic Acid Ethyl Ester A solution of crude 5-(2-methyl-[1,3]dioxolan-2-ylmethyl)-1-(4-nitrobenzyl)-1H-indole-2-carboxylic acid ethyl ester (2.4 g, ≈5 mmol) in dry tetrahydrofuran (20 ml) was shaken in a Parr apparatus with 10% palladium on carbon (200 mg) under 40 psi hydrogen for about four hours. The mixture was filtered and evaporated under reduced pressure to give the title compound (2.03 g), which was reacted without further purification.

PREPARATION 5

1-[4-(2.2.2-Trifluoro-ethanesulfonylamino)-benzyl]-5-(2-methyl-[1,3]dioxolan-2-ylmethyl)-1H-indole-2-carboxylic Acid Ethyl Ester To a solution of crude 1-(4-amino-benzyl)-5-(2-methyl-[1,3]dioxolan-2-ylmethyl)-1H-indole-2-carboxylic acid ethyl ester (2 g, ≈5 mmol) in methylene chloride (25 ml) stirring at about −78° C. under nitrogen was added triethylamine (1.28 g, 1.76 ml, 12.7 mmol). The mixture was stirred for about two minutes, and 2,2,2-trifluoroethanesulfonyl chloride (2.03 g, 1.23 ml, 12.7 mmol) was added dropwise via syringe over about five minutes. The mixture was stirred at about −78° C. for about 45 minutes, then diluted with methylene chloride and water and warmed to room temperature. The organic layer was washed with brine, dried over sodium sulfate, and concentrated in vacuo to an oil. The oil was taken up in methanol (30 ml) and triethylamine (1 ml) and stirred for about two hours at room temperature. The mixture was poured into half-saturated ammonium chloride and extracted into ethyl acetate. The ethyl acetate was washed with brine, dried over sodium sulfate, filtered, and evaporated to give the title compound (2.85 g) as a foam containing some impurities, which was reacted without further purification.

PREPARATION 6

1-[4-(2.2.2-Trifluoro-ethanesulfonylamino)-benzyl]-5-(2-oxo-propyl)-1H-indole-2-carboxylic Acid Ethyl Ester To a solution of crude 1-[4-(2,2,2-trifluoro-ethanesulfonylamino)-benzyl]-5-(2-methyl-[1,3]dioxolan-2-ylmethyl)-1H-indole-2-carboxylic acid ethyl ester (2.85 g, ≈5 mmol) in acetone (60 ml) was added concentrated sulfuric acid (0.6 ml). The solution was stirred at room temperature for about 45 minutes, and most of the solvent was removed under reduced pressure. The residue was taken up in ethyl acetate, washed with water and brine, dried over sodium sulfate, and concentrated in vacuo. The residue was purified by flash chromatography (silica, 130 g) eluting with a gradient from 30% -ethyl acetate/hexane to 40% ethyl acetate/hexane, to give the title compound (1.48 g).

PREPARATION 7

5-[2-(2S-Hydroxy-3-phenoxy-propylamino)-propyl]-1-[4-(2.2.2-trifluoroethanesulfonylamino)-benzyl]-1H-indole-2-carboxylic Acid Ethyl Ester To a solution of 5-[2-(2S-hydroxy-3-phenoxy-propylamino)-propyl]-1-[4-(2,2,2-trifluoro-ethanesulfonylamino)-benzyl]-1H-indole-2-carboxylic acid ethyl ester (1.48 g, 2.98 mmol) and 1-amino-3-phenoxypropan-2(S)-ol (602 mg, 3.6 mmol) in dichloroethane (40 ml) was added powdered sodium sulfate (4.23 g, 29.8 mmol), acetic acid (216 mg, 0.205 ml, 3.6 mmol) and sodium triacetoxyborohydride (947 mg, 4.5 mmol). The mixture was stirred at room temperature under nitrogen for about 4 hours, and then additional 1-amino-3-phenoxypropan-2(S)-ol (200 mg, 1.2 mmol) and sodium triacetoxyborohydride (300 mg, 1.42 mmol) were added. The mixture was stirred for about 16 hours, filtered, and concentrated under reduced pressure. The residue was taken up in ethyl acetate, washed with dilute sodium carbonate and brine, dried over sodium sulfate, filtered, and the solvent was removed in vacuo. The residue was purified by flash chromatography (silica, 105 g), eluting with 5% methanol/methylene chloride, to give the title compound (1.26 g).

We claim:
1. A compound of the formula I

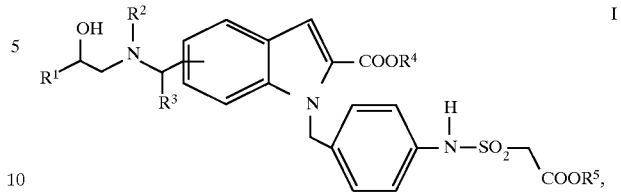

the racemic-enantiomeric mixtures and optical isomers of said compounds, prodrugs thereof and pharmaceutically acceptable salts thereof,
wherein
  $R^1$ is an optionally substituted phenyl, phenoxyalkyl having 1 to 4 carbons in the alkyl portion where the phenoxy portion is optionally substituted;
    where the optionally substituted moieties of $R^1$ are optionally substituted with one to three substituents, each substituent is independently selected from the group consisting of hydroxy, fluoro, chloro, iodo, bromo, nitro, $CF_3$, cyano, sulfonamido, $(C_1-C_6)$ alkyl optionally independently substituted with one or more halo atoms, $(C_1-C_6)$alkoxy optionally independently substituted with one or more halo atoms, carboxy, $(C_1-C_4)$alkoxycarbonyl, $(C_1-C_6)$alkylthio, sulfonyl, sulfinyl, —$NX^1X^2$, —NH—CO—$(CH_2)_a$-(phenyl), —NH—CO—$(C_1-C_{10})$alkyl, —NH—$SO_2$—$(CH_2)_a$-(phenyl) and —NH—$SO_2$—$(C_1-C_{10})$ alkyl;
  a for each occurrence is independently 0, 1, 2, 3 or 4;
  $X^1$ and $X^2$ for each occurrence are each independently hydrogen, $(C_1-C_6)$alkyl, $(C_1-C_8)$alkoxy$(C_1-C_6)$ alkyl, or $(C_3-C_8)$cycloalkyl;
  $R^2$ is hydrogen or $(C_1-C_6)$alkyl;
  $R^3$ is hydrogen or $(C_1-C_6)$alkyl optionally independently substituted with one or more halo atoms;
  $R^4$ is hydrogen or $(C_1-C_4)$alkyl optionally independently substituted with one or more halo atoms; and
  $R^5$ is hydrogen or $(C_1-C_4)$alkyl.
2. A compound according to claim 1 wherein $R^1$ is phenoxyalkyl having 1 to 4 carbons in the alkyl portion.
3. A compound according to claim 2 wherein $R^2$ is hydrogen.
4. A compound according to claim 3 wherein $R^3$ is $(C_1-C_6)$alkyl.
5. A compound according to claim 4 wherein $R^4$ is hydrogen, methyl or ethyl.
6. A compound according to claim 5 wherein $R^1$ is phenoxymethylene.
7. A compound according to claim 6 wherein $R^3$ is methyl.
8. A compound according to claim 7 wherein $R^5$ is hydrogen or methyl.
9. The compound according to claim 1 of the formula

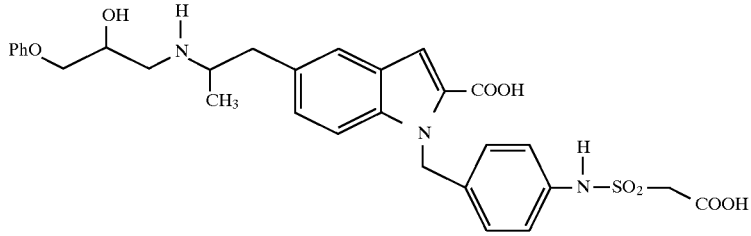

10. The compound according to claim 1 of the formula

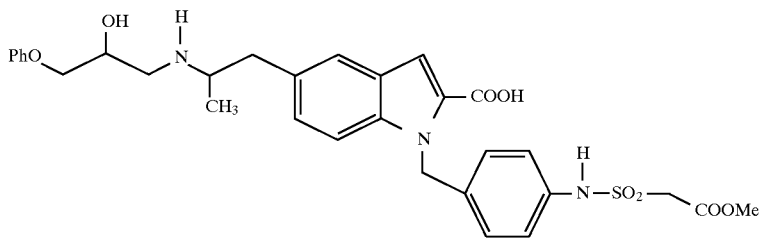

11. A pharmaceutical composition comprising a compound according to claim 1, or a prodrug thereof, or a pharmaceutically acceptable salt of said compound or prodrug and a pharmaceutically acceptable carrier.

12. A method of treating a condition selected from the group consisting of diabetes, hyperglycemia and obesity in a mammal, comprising administering to a mammal in need of such treatment an effective amount of a compound of formula (I), or a prodrug thereof, or a pharmaceutically acceptable salt of said compound or prodrug, according to claim 1.

13. A method of increasing the content of lean meat in animals comprising administering to an animal an effective amount of a compound of formula (I), or a prodrug thereof, or a pharmaceutically acceptable salt of said compound or prodrug, according to claim 1.

14. A method for treating prostate disease in a mammal comprising administering to a mammal in need of such treatment an effective amount of a compound of formula (I), or a prodrug thereof, or a pharmaceutically acceptable salt of said compound or prodrug according to claim 1.

15. A method of treating intestinal motility disorders in a mammal comprising administering to a mammal in need of such treatment an effective amount of a compound of formula (I), or a prodrug thereof, or a pharmaceutically acceptable salt of said compound or prodrug according to claim 1.

16. A method of treating depression in a mammal comprising administering to a mammal in need of such treatment an effective amount of a compound of formula (I), or a prodrug thereof, or a pharmaceutically acceptable salt of said compound or prodrug according to claim 1.

17. A method of treating dyslipidemia in a mammal comprising administering to a mammal in need of such treatment an effective amount of a compound of formula (I), or a prodrug thereof, or a pharmaceutically acceptable salt of said compound or prodrug according to claim 1.

18. A method for treating airway inflammatory disorders in a mammal comprising administering to a mammal in need of such treatment an effective amount of a compound of formula (I), or a prodrug thereof, or a pharmaceutically acceptable salt of said compound or prodrug according to claim 1.

19. A feed premix comprising a compound according to claim 1, or a prodrug thereof, or a pharmaceutically acceptable salt of said compound or prodrug and one or more carriers.

20. A high potency concentrate comprising a compound according to claim 1, or a prodrug thereof, or a pharmaceutically acceptable salt of said compound or prodrug and one or more carriers.

* * * * *